United States Patent [19]
Kamboj et al.

[11] Patent Number: 6,040,175
[45] Date of Patent: Mar. 21, 2000

[54] AMPA-BINDING HUMAN GLUR2 RECEPTORS

[75] Inventors: Rajender Kamboj, Mississauga; Candace E. Elliott; Stephen L. Nutt, both of Etobicoke, all of Canada

[73] Assignee: Allelix Biopharmaceuticals, Inc., Mississauga, Canada

[21] Appl. No.: 08/483,327

[22] Filed: Jun. 7, 1995

Related U.S. Application Data

[62] Division of application No. 08/242,344, May 13, 1994, which is a continuation of application No. 07/896,437, Jun. 10, 1992, abandoned.

[51] Int. Cl.[7] .............................. C07K 14/705; C12N 5/10
[52] U.S. Cl. .......................... 435/325; 530/350; 530/300; 424/185.1; 435/69.1; 435/252.3; 435/254.11
[58] Field of Search ..................................... 530/350, 300, 530/806; 536/23.5; 435/240.2, 252.3, 254.11, 325; 424/185.1

[56] References Cited

U.S. PATENT DOCUMENTS

| | | | |
|---|---|---|---|
| 5,202,257 | 4/1993 | Heinemann et al. | 435/252.3 |
| 5,521,297 | 5/1996 | Daggett et al. | 536/23.5 |
| 5,610,032 | 3/1997 | Kamboj et al. | 435/69.1 |
| 5,643,785 | 7/1997 | Kamboj et al. | 435/325 |

FOREIGN PATENT DOCUMENTS

91/06648  5/1991  WIPO .

OTHER PUBLICATIONS

McNamara et al. "Chromosomal Localization of Human Glutamate Receptor Genes", *Jnl. of Neurosci.*, 12(7):2555–2562, Jul., 1992.
Hollmann et al, Nature 1989 342:643.
Keinanen et al, Science 1990 249:556.
Boulter et al, Science 1990 249:1033.
Bettler et al, Neuron 1990 5:583.
Monyer et al, Neuron 1991 6:799.
Nakanishi et al, Neuron 1990 5:569.
Hollmann et al, Science 1991 252:851.
Verdoorn et al, Science 1991 252:1715.
Egebjerg et al, Nature 1991 351:745.
Wada et al, Nature 1989 342:684.
Gregor et al, Nature 1989 342:689.
Werner et al, Nature 1991 351:742.
Barnett et al, Nucleic Acids Res. 1990 18(10):3094.
W. Sun et al., "Molecular Cloning, Chromosomal Mapping, and Functional Expression of Human Brain Glutamate Receptors", Proc. Natl. Acad. Sci. USA, vol. 89, pp. 1443–1447, Feb. 1992.
C. Puckett, et al., "Moleuclar Cloning and Chromosomal Localization of One of the Human Glutamate Receptor Genes", Proc. Natl. Acad. Sci. USA, vol. 88, pp. 7557–7561, Sep. 1991.
Sakimura et al., Functional expression from cloned cDNAs of glutamate receptor species responsive to kainate and quisqualate, FEBS Lett. 272(1,2): 73–80, Oct. 1990.
Gallo et al., Molecular cloning and developmental analysis of a new glutamate receptor subunit isoform in cerebellum, J. Neurosci., 12(3): 1010–1023, Mar. 1992.
Lerner, R.A., Antibodies of predetermined specificity in biology and medicine, Adv. Immunol. 36: 1–44, 1984.
Sommer et al., Flip and flop: a cell–specific functional switch in glutamate–operated channels of the CNS, Science, 249: 1580–1585, Sep. 1990.
Hudziak et al., Mol. Cell. Biol., 9(3):1165–1172, Mar. 1989.

*Primary Examiner*—Lorraine Spector
*Assistant Examiner*—Claire M. Kaufman
*Attorney, Agent, or Firm*—Foley & Lardner

[57] ABSTRACT

Described herein are isolated polynucleotides which code for an AMPA-type human CNS glutamate receptor, designated the human GluR2B receptor. The receptor is characterized structurally and the construction and use of cell lines expressing these receptor is disclosed.

9 Claims, 14 Drawing Sheets

FIG. I(A)

EcoRI
--
```
1    GAATTCCGTGAGTGCATGGGAGGGTGCTGAATATTCCGAGACACTGGACCACAGCGGCA    60
     ----------+---------+---------+---------+---------+---------+
     CTTAAGGCACTCACGTACCCTCCCACGACTTATAAGGCTCTGTGACCCTGGTGTCGCCGT

61   GCTCCGCTGAAAACTGCATTCAGCCAGTCCTCCGGACTTCTGGAGCGGGGACAGGGCGCA   120
     ----------+---------+---------+---------+---------+---------+
     CGAGGCGACTTTTGACGTAAGTCGGTCAGGAGGCCTGAAGACCTCGCCCCTGTCCCGCGT

121  GGGCATCAGCAGCCACCAGCAGGACCTGGGAAATAGGGATTCTTCTGCCTCCACTTCAGG   180
     ----------+---------+---------+---------+---------+---------+
     CCCGTAGTCGTCGGTGGTCGTCCTGGACCCTTTATCCCTAAGAAGACGGAGGTGAAGTCC

181  TTTTAGCAGCTTGGTGCTAAATTGCTGTCTCAAAATGCAGAGGATCTAATTGCAGAGGA    240
     ----------+---------+---------+---------+---------+---------+
     AAAATCGTCGAACCACGATTTAACGACAGAGTTTTACGTCTCCTAGATTAAACGTCTCCT

241  AAACAGCCAAAGAAGGAAGAGGAAAAGGGGTATATTGTGGATGCTC                 300
     ----------+---------+---------+---------+---------+---------+
     TTTGTCGGTTTCTTCCTTCTCCTTTTTTTCCCCATATAACACCTACGAG

301  TACTTTTCTTGGAAATGCAAAAGATTATGCATATTTCTGTCCTCCTTTCTCCTGTTTTAT  360
     ----------+---------+---------+---------+---------+---------+
     ATGAAAAGAACCTTTACGTTTTCTAATACGTATAAAGACAGGAGGAAAGAGGACAAAATA

```
     GGGGACTGATTTTGGTGTCTCTTCTAACAGCATACAGATAGGGGGGCTATTCCTAGGG
361  -------+---------+---------+---------+---------+---------+ 420
     CCCCTGACTAAAACCACAGAGAAGATTGTCGTATGTCTATCCCCCGATAAGGATCCC

G  L  I  F  G  V  S  S  N  S  I  Q  I  G  G  L  F  P  P  R  G  -
                                |_Mature N-Terminal GCGCCGATCAAGAATACAGTGCATTCGAGTAGGAGGATGGTTCAGTTTTCCACTTCGGAGT
421  -------+---------+---------+---------+---------+---------+ 480
     CGCGGCTAGTTCTTATGTCACGTAAAGCTCATCCTACCAAGTCAAAAGGTGAAGCCTCA

A  D  Q  E  Y  S  A  F  R  V  G  M  V  Q  F  S  T  S  E  F  -

TCAGACTGACACCCCACATGACAATTGGAGGTGGCAAACAGCTTCGCAGTCACTAATG
481  -------+---------+---------+---------+---------+---------+ 540
     AGTCTGACTGTGGGGTGTAGCTGTTAACCTCCACGTTTGTCGAAGCGTCAGTGATTAC

R  L  T  P  H  I  D  N  L  E  V  A  N  S  F  A  V  T  N  A  -

CTTTCTGCTCCCAGTTTTCGAGAGGAGTCTATGCTATTTTTGGATTTTATGACAAGAAGT
541  -------+---------+---------+---------+---------+---------+ 600
     GAAAGACGAGGGTCAAAAGCTCTCCTCAGATACGATAAAAACCTAAAATACTGTTCTTCA

F  C  S  Q  F  S  R  G  V  Y  A  I  F  G  F  Y  D  K  K  S  -

CTGTAAATACCATCACATCATTTGCGGAACACTCCACGTCTCCTTCATCACTCCCAGCT
601  -------+---------+---------+---------+---------+---------+ 660
     GACATTTATGGTAGTGTAGTAAAACGCCTTGTGAGGTGCAGAGAAGTAGTGAGGGTCGA

```
     TCCCAACAGATGGCACACATCCATTTGTCATTCAGATGAGACCCGACCTCAAAGGAGCTC
661  ------+---------+---------+---------+---------+---------+   720
     AGGGTTGTCTACCGTGTGTAGGTAAACAGTAAGTCTACTCTGGGCTGGAGTTTCCTCGAG

P  T  D  G  T  H  P  F  V  I  Q  M  R  P  D  L  K  G  A  L  -

TCCTTAGCTTGATTGAATACTATCAATGGGACAAGTTTGCATACCCTCTATGACAGTGACA
721  ------+---------+---------+---------+---------+---------+   780
     AGGAATCGAACTAACTTATGATAGTTACCCTGTTCAAACGTATGGAGATACTGTCACTGT

L  S  L  I  E  Y  Y  Q  W  D  K  F  A  Y  L  Y  D  S  D  R  -

GAGGCTTATCAACACTGCAAGCTGTGCTGGATTCTGCTGCTGAAAAGAAATGGCAAGTGA
781  ------+---------+---------+---------+---------+---------+   840
     CTCCGAATAGTTGTGACGTTCGACACGACCTAAGACGACGACTTTTCTTTACCGTTCACT

G  L  S  T  L  Q  A  V  L  D  S  A  A  E  K  K  W  Q  V  T  -

CTGCTATCAATGTGGGAAACATTAACAATGACAAGAAAGATGAGATGTACCGATCACTTT
841  ------+---------+---------+---------+---------+---------+   900
     GACGATAGTTACACCCTTTGTAATTGTTACTGTTCTTTCTACTCTACATGGCTAGTGAAA

A  I  N  V  G  N  I  N  N  D  K  K  D  E  M  Y  R  S  L  F  -

TTCAAGATCTGGAGTTAAAAAAGGAACGGCGTGTAATTCTGGACTGTGAAAGGGATAAAG
901  ------+---------+---------+---------+---------+---------+   960
     AAGTTCTAGACCTCAATTTTTTCCTTGCCGCACATTAAGACCTGACACTTTCCCTATTTC
```

FIG. I(D)

```
       Q  D  L  E  L  K  K  E  R  R  V  I  L  D  C  E  R  D  K  V  -
      TAAACGACATTGTAGACCAGGTTATTACCATTGGAAAACACGTTAAAGGTACCACTACA
 961  ------+---------+---------+---------+---------+---------+  1020
      ATTTGCTGTAACATCTGGTCCAATAATGGTAACCTTTTGTGCAATTCCCATGGTGATGT
       N  D  I  V  D  Q  V  I  T  I  G  K  H  V  K  G  Y  H  Y  I  -

TCATTGCAAATCTGGGATTACTGATGGAGACCTATTAAAAATCCAGTTTGGAGGTGCAA
1021  ------+---------+---------+---------+---------+---------+  1080
      AGTAACGTTTAGACCCTAATGACTACCTCTGGATAATTTTTAGGTCAAACCTCCACGTT
       I  A  N  L  G  F  T  D  G  D  L  L  K  I  Q  F  G  G  A  N  -

ATGTCTCTGGATTTCAGATAGTGTGGACTATGATGATTCGTTGGTATCTAAATTTATAGAAA
1081  ------+---------+---------+---------+---------+---------+  1140
      TACAGAGACCTAAAGTCTATCACCTGATACTACTAAGCAACCATAGATTTAAATATCTTT
       V  S  G  F  Q  I  V  D  Y  D  D  S  L  V  S  K  F  I  E  R  -

GATGGTCAACACTGGAAGAAAAAGAATACCCTGGAGCTCACACAACAATTAAGTATA
1141  ------+---------+---------+---------+---------+---------+  1200
      CTACCAGTTGTGACCTTCTTTTTCTTATGGGACCTCGAGTGTGTTGTTAATTCATAT
       W  S  T  L  E  E  K  E  Y  P  G  A  H  T  T  I  K  Y  T  -

CTTCTGCTCTGACCTATGATGCCGTTCAAGTGATGACTGAAGCCTTCCGCAACCTAAGGA
1201  ------+---------+---------+---------+---------+---------+  1260
      GAAGACGAGACTGGATACTACGGCAAGTTCACTACTGACTTCGGAAGGCGTTGGATTCCT
       S  A  L  T  Y  D  A  V  Q  V  M  T  E  A  F  R  N  L  R  K  -
```

FIG. I(E)

```
1261 AGCAAAGAATTGAAATCTCCCGAAGGGGGAATGCAGGAGACTGTCTGGCAAACCCAGCAG
     ------+---------+---------+---------+---------+---------+   1320
     TCGTTTCTTAACTTTAGAGGGCTTCCCCCCTTACGTCCTCTGACAGACCGTTGGGTCGTC
      Q  R  I  E  I  S  R  R  G  N  A  G  D  C  L  A  N  P  A  V  -

1321 TGCCCTGGGGACAAGGTGTAGAAATAGAAAGGGCCCTCAAACAGGTTCAGGTTGAAGGTC
     ------+---------+---------+---------+---------+---------+   1380
     ACGGGACCCCTGTTCCACATCTTTATCTTTCCCGGGAGTTTGTCCAAGTCCAACTTCCAG
      P  W  G  Q  G  V  E  I  E  R  A  L  K  Q  V  Q  V  E  G  L  -

1381 TCTCAGGAAATATAAAGTTTGACCAGAATGGGAAAAGAATAAACTATACAATTAACATCA
     ------+---------+---------+---------+---------+---------+   1440
     AGAGTCCTTTATATTTCAAACTGGTCTTACCCTTTTTCTTATTTGATATGTTAATTGTAGT
      S  G  N  I  K  F  D  Q  N  G  K  R  I  N  Y  T  I  N  I  M  -

1441 TGGAGCTCAAAACTAATGGGCCCCGGAAGATTGGCTACTGGAGTGAAGTGGACAAAATGG
     ------+---------+---------+---------+---------+---------+   1500
     ACCTCGAGTTTTGATTACCCGGGGCCTTCTAACCGATGACCTCACTTCACCTGTTTTACC
      E  L  K  T  N  G  P  R  K  I  G  Y  W  S  E  V  D  K  M  V  -

1501 TTGTTACCCTTACTGAGCTCCCTTCTGGAAATGACACCTCTGGGCTTGAGAATAAGACTG
     ------+---------+---------+---------+---------+---------+   1560
     AACAATGGGAATGACTCGAGGGAAGACCTTTACTGTGGAGACCCGAACTCTTATTCTGAC
      V  T  L  T  E  L  P  S  G  N  D  T  S  G  L  E  N  K  T  V  -
```

FIG. 1(F)

```
      TTGTTGTCACCACAATTTGGAATCTCCGTATGTTATGATGAAGAAAAATCATGAAATGC
1561  ----------+---------+---------+---------+---------+---------+  1620
      AACAACAGTGGTGTTAAACCTTAGAGGCATACAATACTACTTCTTTTTAGTACTTTACG

V  V  T  T  I  L  E  S  P  Y  V  M  M  K  K  N  H  E  M  L

TTGAAGGCAATGAGGCGCTATGAGGGCTACTGTGTTGACCTGGCTGCAGAAATCGCCAAAC
1621  ----------+---------+---------+---------+---------+---------+  1680
      AACTTCCGTTACTCCGCGATACTCCCGATGACACAACTGGACCGACGTCTTTAGCGGTTTG

E  G  N  E  R  Y  E  G  Y  C  V  D  L  A  A  E  I  A  K  H

ATTGTGGGTTCAAGTACAAGTTGACAATTGTTGGTGATGGCAAGTATGGGCCAGGGATG
1681  ----------+---------+---------+---------+---------+---------+  1740
      TAACACCCAAGTTCATGTTCAACTGTTAACAACCACTACCGTTCATACCCGGTCCCTAC

C  G  F  K  Y  K  L  T  I  V  G  D  D  G  K  Y  G  A  R  D  A

CAGACACGAAAATTTGGAATGGGGAGAACTTGTATATGGAAAGCTGATATTG
1741  ----------+---------+---------+---------+---------+---------+  1800
      GTCTGTGCTTTTAAACCTTACCAACCTCTTGAACATATACCCTTTCGACTATAAC

D  T  K  I  W  N  G  M  V  G  E  L  V  Y  G  K  A  D  I  A

CAATTGCTCCATTAACTATTACCCTTGTGAGAGAAGAGGTGATTGACTTCTCAAAGCCCT
1801  ----------+---------+---------+---------+---------+---------+  1860
      GTTAACGAGGTAATTGATAATGGGAACACTCTCTTCTCCACTAACTGAAGAGTTTCGGGA

```
      TCATGAGCCTCGGGATATCTATCATGATCAAGAAGCCTCAGAAGTCCAAACCAGGAGTGT
1861  ------------+---------+---------+---------+---------+--------- 1920
      AGTACTCGGAGCCCTATAGATAGTACTAGTTCTTCGGAGTCTTCAGGTTTGGTCCTCACA

M  S  L  G  I  S  I  M  I  K  K  P  Q  K  S  K  P  G  V  F  -

TTTCCTTTCTTGATCCTTTAGCCTATGAGATCTGGATGTGCATTGTTTTTGCCTACATTG
1921  ------------+---------+---------+---------+---------+--------- 1980
      AAAGGAAAGAACTAGGAAATCGGATACTCTAGACCTACACGTAACAAAAACGGATGTAAC

S  F  L  D  P  L  A  Y  E  I  W  M  C  I  V  F  A  Y  I  G  -

GGGTCAGTGTAGTTTTATTCCTGGTCAGCAGATTTAGCCCCTACGAGTGGCACACTGAGG
1981  ------------+---------+---------+---------+---------+--------- 2040
      CCCAGTCACATCAAAATAAGGACCAGTCGTCTAAATCGGGGATGCTCACCGTGTGACTCC

V  S  V  V  L  F  L  V  S  R  F  S  P  Y  E  W  H  T  E  E  -

AGTTTGAAGATGGAAGAGAAACACAAAGTAGTGAATCAACTAATGAATTTGGGATTTTTA
2041  ------------+---------+---------+---------+---------+--------- 2100
      TCAAACTTCTACCTTCTCTTTGTGTTTCATCACTTAGTTGATTACTTAAACCCTAAAAAT

F  E  D  G  R  E  T  Q  S  S  E  S  T  N  E  F  G  I  F  N  -

ATAGTCTCTGGTTTTCCTTGGGTGCCTTTATGCGGCAAGGATGCCGATATTCGCCAAGAT
2101  ------------+---------+---------+---------+---------+--------- 2160
      TATCAGAGACCAAAAGGAACCCACGGAAATACGCCGTTCCTACGCTATAAGCGGTTCTA

```
2161  CCCTCTCTGGGCGCATTGTTGGAGGTGTGTGGTTCTTTACCCTGATCATAATCTCCT
      ---------+---------+---------+---------+---------+---------+  2220
      GGGAGAGACCCGCGTAACAACCTCCACACACCAAGAAATGGGACTAGTATTAGAGA

L  S  G  R  I  V  G  G  V  W  W  F  F  T  L  I  I  I  S  -

2221  CCTACACGGCTAACTTAGCTGCCTTCCTGACTGTAGAGAGGATGGTGTCTCCCATCGAAA
      ---------+---------+---------+---------+---------+---------+  2280
      GGATGTGCCGATTGAATCGACGGAAGGACTGACATCTCTCCTACCACAGAGGGTAGCTTT

Y  T  A  N  L  A  A  F  L  T  V  E  R  M  V  S  P  I  E  S  -

2281  GTGCTGAGGATCTTTCTAAGCAAACAGAATCTAAAATTGCTTATGGAACATTAGACTCTGGCTCCA
      ---------+---------+---------+---------+---------+---------+  2340
      CACGACTCCTAGAAAGATTCGTTTGTCTTAGATTTTAACGAATACCTTGTAATCTGAGACCGAGT

A  E  D  L  S  K  Q  T  E  I  A  Y  G  T  L  D  S  G  S  T  -

2341  CTAAAGAGTTTTTCAGGAGATCTAAAATTGCAGTGTTTGATAAAATGTGGACCTACATGC
      ---------+---------+---------+---------+---------+---------+  2400
      GATTTCTCAAAAAGTCCTCTAGATTTAACGTCACAAACTATTTTACACCTGGATGTACG

K  E  F  F  R  R  S  K  I  A  V  F  D  K  M  W  T  Y  M  R  -

2401  GGAGTGCGGAGCCCTCTGTGTTTGTGAGGACTACGGCCGAAGGGGTGGCTAGAGTGCCGA
      ---------+---------+---------+---------+---------+---------+  2460
      CCTCACGCCTCGGGAGACACAAACACTCCTGATGCCGGCTTCCCCACCGATCTCACGCCT

```
2461  AGTCCAAAGGGAAATATGCCTACTTGTTGGAGTCCACGATGAACGAGTACATTGAGCAAA
      ----------+---------+---------+---------+---------+---------+ 2520
      TCAGGTTTCCCTTTATACGGATGAACAACCTCAGTGCTACTTGCTCATGTAACTCGTTT

S   K   G   K   Y   A   Y   L   L   E   S   T   M   N   E   Y   I   E   Q   R  -

2521  GGAAGCCTTGCGACACCATGAAAGTTGGTGGAAACCTGGATTCCAAAGGCTATGGCATCG
      ----------+---------+---------+---------+---------+---------+ 2580
      CCTTCGGAACGCTGTGGTACTTTCAACCACCTTTGGACCTAAGGTTTCCGATACCGTAGC

K   P   C   D   T   M   K   V   G   G   N   L   D   S   K   G   Y   G   I   A  -

2581  CAACACCTAAAGGATCCTCATTAGGAACCCCAGTAAATCTTGCAGTATTGAAACTCAGTG
      ----------+---------+---------+---------+---------+---------+ 2640
      GTTGTGGATTTCCTAGGAGTAATCCTTGGGGTCATTTAGAACGTCATAACTTTGAGTCAC

T   P   K   G   S   S   L   G   T   P   V   N   L   A   V   L   K   L   S   E  -

2641  AGCAAGGCGTCTTAGACAAGCTGAAAAACAAATGTGGTACGATAAAGGTGAATGTGGAG
      ----------+---------+---------+---------+---------+---------+ 2700
      TCGTTCCGCAGAATCTGTTCGACTTTTTGTTTACCACCATGCTATTTCCACTTACACCTC

Q   G   V   L   D   K   L   K   N   K   W   W   Y   D   K   G   E   C   G   A  -

2701  CCAAGGACTCTGGAAGTAAGGAAAAGACCAGTGCCCTCAGTCTGAGCAACGTTGCTGGAG
      ----------+---------+---------+---------+---------+---------+ 2760
      GGTTCCTGAGACCTTCATTCCTTTTCTGGTCACGGGAGTCAGACTCGTTGCAACGACCTC

```
2761  TATTCTACATCCTTGTCGGGGGCCTTGGTTTGGCAATGCTGGTGGCCTTTGATTGAGTTCT
      ----------+---------+---------+---------+---------+---------+  2820
      ATAAGATGTAGGAACAGCCCCCGGAACCAAACCGTTACGACCACCGAAACTAACTCAAGA

F  Y  I  L  V  G  G  L  G  L  A  M  L  V  A  L  I  E  F  C  -

2821  GTTACAAGTCAAGGGCCGAGGGCGAAACGAATGAAGGTGGCAAAGAATGCACAGAATATTA
      ----------+---------+---------+---------+---------+---------+  2880
      CAATGTTCAGTTCCCGGCTCCCGCTTTGCTTACTTCCACCGTTTCTTACGTGTCTTATAAT

Y  K  S  R  A  E  A  K  R  M  K  V  A  K  N  A  Q  N  I  N  -
                             EcoRI
                             ---

2881  ACCCATCTTCCTCGCAGAATTCACAGAATTTGCAACTTATAAGGAAGGTTACAACGTAT
      ----------+---------+---------+---------+---------+---------+  2940
      TGGGTAGAAGGAGCGTCTTAAGTGTCTTAAACGTTGAATATTCCTTCCAATGTTGCATA

P  S  S  Q  N  S  Q  N  F  A  T  Y  K  E  G  Y  N  V  Y  -

2941  ATGGCATCGAAAGTGTTAAAAATTTAGGGGATGACCTTGAATGATGCCATGAGGAACAAGG
      ----------+---------+---------+---------+---------+---------+  3000
      TACCGTAGCTTTCACAATTTTTAAATCCCCTACTGGAACTTACTACGGTACTCCTTGTTCC

G  I  E  S  V  K  I  *

3001  CAAGGCTGTCAATTACAGGAAGTACTGGAGAAAATGGACGTGTTATGACTCCAGAATTTC
      ----------+---------+---------+---------+---------+---------+  3060
      GTTCCGACAGTTAATGTCCTTCATGACCTCTTTTACCTGCACAATACTGAGGTCTTAAAG
```

FIG. I(K)

```
3061 CCAAAGCNGTGCATGCTGTCCCTTACGTGAGTCCTGGCATGGGAATGAATGTCAGTGTGA 3120
     ||||||||||||||||||||||||||||||||||||||||||||||||||||||||||||
     GGTTTCGNCACGTACGACAGGGAATGCACTCAGGACCGTACCCTTACTTACAGTCACACT

3121 CTGATCTCTCGTGATTGATAAGAACCTTTGAGTGCCTTACACAATGGTTTCTTGTGTG 3180
     ||||||||||||||||||||||||||||||||||||||||||||||||||||||||||||
     GACTAGAGAGCACTAACTATTCTTGGAAAACTCACGGAATGTGTTACCAAAAGAACACAC

EcoRI
                                            --
3181 TTTATTGTCAAAGTGGTGAGAGGCATCCAGTATCTTGAAGACTTTTCTTTCAGCCAAGAA 3240
     ||||||||||||||||||||||||||||||||||||||||||||||||||||||||||||
     AAATAACAGTTTCACCACTCTCCGTAGGTCATAGAACTTCTGAAAAGAAAGTCGGTTCTT

3241 TTCTTAAATATGTGGAGTTCATCTTGAATTGTAAGGAATGATTAATTAAAACACAACATC 3300
     ||||||||||||||||||||||||||||||||||||||||||||||||||||||||||||
     AAGAATTTATACACCTCAAGTAGAACTTAACATTCCTTACTAATTAATTTGTGTTGTAG

3301 TTTTTCTACTCGAGTTACAGACAAAGCGTGGTGGACATGCACAGCTAACATGGAAGTACT 3360
     ||||||||||||||||||||||||||||||||||||||||||||||||||||||||||||
     AAAAAGATGAGCTCAATGTCTGTTTCGCACCACCTGTACGTGTCGATTGTACCTTCATGA

3361 ATAATTTACCTGAAGTCTTTGTACAGACAACAAACCTGTTTCTGCAG 3407
     |||||||||||||||||||||||||||||||||||||||||||||||
     TATTAAATGGACTTCAGAAACATGTCTGTTGTTTGGACAAAGACGTC
```

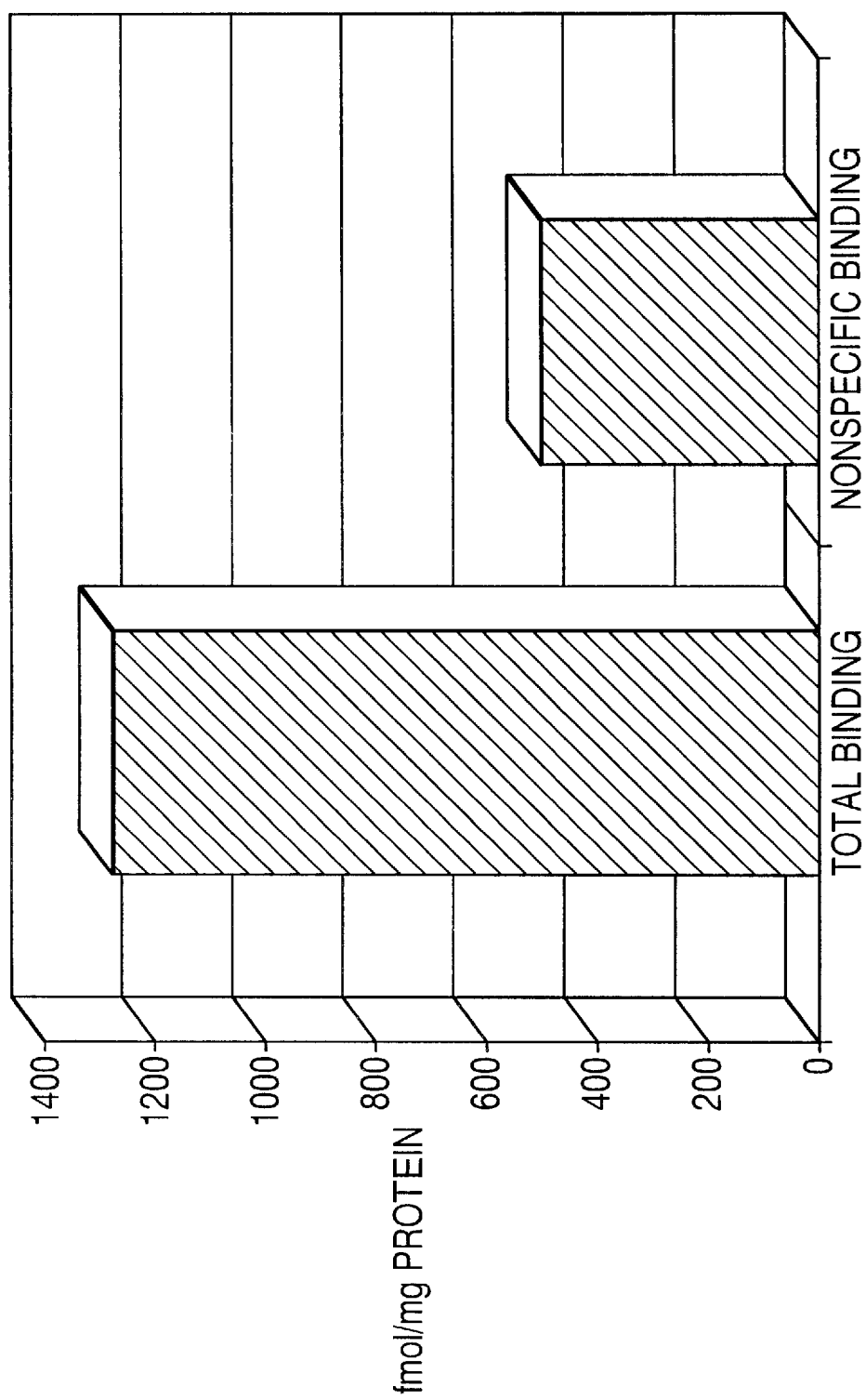

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 3407 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 315..2966

(ix) FEATURE:
      (A) NAME/KEY: sig_peptide
      (B) LOCATION: 315..374

(ix) FEATURE:
      (A) NAME/KEY: mat_peptide
      (B) LOCATION: 375..2966

(xi) SEQUENCE DESCRIPTION: SEQ ID NO:1:

```
GAATTCCGTG AGTGCATGGG AGGGTGCTGA ATATTCCGAG ACACTGGGAC CACAGCGGCA        60

GCTCCGCTGA AAACTGCATT CAGCCAGTCC TCCGGACTTC TGGAGCGGGG ACAGGGCGCA       120

GGGCATCAGC AGCCACCAGC AGGACCTGGG AAATAGGGAT TCTTCTGCCT CCACTTCAGG       180

TTTTAGCAGC TTGGTGCTAA ATTGCTGTCT CAAAATGCAG AGGATCTAAT TTGCAGAGGA       240
```

-continued

```
AAACAGCCAA AGAAGGAAGA GGAGGAAAAG GAAAAAAAAA GGGGTATATT GTGGATGCTC        300

TACTTTTCTT GGAA ATG CAA AAG ATT ATG CAT ATT TCT GTC CTC CTT TCT         350
          Met Gln Lys Ile Met His Ile Ser Val Leu Leu Ser
          -20              -15                  -10

CCT GTT TTA TGG GGA CTG ATT TTT GGT GTC TCT TCT AAC AGC ATA CAG         398
Pro Val Leu Trp Gly Leu Ile Phe Gly Val Ser Ser Asn Ser Ile Gln
        -5                  1                5

ATA GGG GGG CTA TTT CCT AGG GGC GCC GAT CAA GAA TAC AGT GCA TTT         446
Ile Gly Gly Leu Phe Pro Arg Gly Ala Asp Gln Glu Tyr Ser Ala Phe
        10              15                  20

CGA GTA GGG ATG GTT CAG TTT TCC ACT TCG GAG TTC AGA CTG ACA CCC         494
Arg Val Gly Met Val Gln Phe Ser Thr Ser Glu Phe Arg Leu Thr Pro
25              30                  35                  40

CAC ATC GAC AAT TTG GAG GTG GCA AAC AGC TTC GCA GTC ACT AAT GCT         542
His Ile Asp Asn Leu Glu Val Ala Asn Ser Phe Ala Val Thr Asn Ala
                45                  50                  55

TTC TGC TCC CAG TTT TCG AGA GGA GTC TAT GCT ATT TTT GGA TTT TAT         590
Phe Cys Ser Gln Phe Ser Arg Gly Val Tyr Ala Ile Phe Gly Phe Tyr
                    60                  65                  70

GAC AAG AAG TCT GTA AAT ACC ATC ACA TCA TTT TGC GGA ACA CTC CAC         638
Asp Lys Lys Ser Val Asn Thr Ile Thr Ser Phe Cys Gly Thr Leu His
            75                  80                  85

GTC TCC TTC ATC ACT CCC AGC TTC CCA ACA GAT GGC ACA CAT CCA TTT         686
Val Ser Phe Ile Thr Pro Ser Phe Pro Thr Asp Gly Thr His Pro Phe
        90                  95                  100

GTC ATT CAG ATG AGA CCC GAC CTC AAA GGA GCT CTC CTT AGC TTG ATT         734
Val Ile Gln Met Arg Pro Asp Leu Lys Gly Ala Leu Leu Ser Leu Ile
105                 110                 115                 120

GAA TAC TAT CAA TGG GAC AAG TTT GCA TAC CTC TAT GAC AGT GAC AGA         782
Glu Tyr Tyr Gln Trp Asp Lys Phe Ala Tyr Leu Tyr Asp Ser Asp Arg
                125                 130                 135

GGC TTA TCA ACA CTG CAA GCT GTG CTG GAT TCT GCT GCT GAA AAG AAA         830
Gly Leu Ser Thr Leu Gln Ala Val Leu Asp Ser Ala Ala Glu Lys Lys
                140                 145                 150

TGG CAA GTG ACT GCT ATC AAT GTG GGA AAC ATT AAC AAT GAC AAG AAA         878
Trp Gln Val Thr Ala Ile Asn Val Gly Asn Ile Asn Asn Asp Lys Lys
        155                 160                 165

GAT GAG ATG TAC CGA TCA CTT TTT CAA GAT CTG GAG TTA AAA AAG GAA         926
Asp Glu Met Tyr Arg Ser Leu Phe Gln Asp Leu Glu Leu Lys Lys Glu
        170                 175                 180

CGG CGT GTA ATT CTG GAC TGT GAA AGG GAT AAA GTA AAC GAC ATT GTA         974
Arg Arg Val Ile Leu Asp Cys Glu Arg Asp Lys Val Asn Asp Ile Val
185                 190                 195                 200

GAC CAG GTT ATT ACC ATT GGA AAA CAC GTT AAA GGG TAC CAC TAC ATC        1022
Asp Gln Val Ile Thr Ile Gly Lys His Val Lys Gly Tyr His Tyr Ile
                205                 210                 215

ATT GCA AAT CTG GGA TTT ACT GAT GGA GAC CTA TTA AAA ATC CAG TTT        1070
Ile Ala Asn Leu Gly Phe Thr Asp Gly Asp Leu Leu Lys Ile Gln Phe
                220                 225                 230

GGA GGT GCA AAT GTC TCT GGA TTT CAG ATA GTG GAC TAT GAT GAT TCG        1118
Gly Gly Ala Asn Val Ser Gly Phe Gln Ile Val Asp Tyr Asp Asp Ser
            235                 240                 245

TTG GTA TCT AAA TTT ATA GAA AGA TGG TCA ACA CTG GAA GAA AAA GAA        1166
Leu Val Ser Lys Phe Ile Glu Arg Trp Ser Thr Leu Glu Glu Lys Glu
        250                 255                 260

TAC CCT GGA GCT CAC ACA ACA ACA ATT AAG TAT ACT TCT GCT CTG ACC        1214
Tyr Pro Gly Ala His Thr Thr Thr Ile Lys Tyr Thr Ser Ala Leu Thr
265                 270                 275                 280
```

-continued

```
TAT GAT GCC GTT CAA GTG ATG ACT GAA GCC TTC CGC AAC CTA AGG AAG        1262
Tyr Asp Ala Val Gln Val Met Thr Glu Ala Phe Arg Asn Leu Arg Lys
                285                 290                 295

CAA AGA ATT GAA ATC TCC CGA AGG GGG AAT GCA GGA GAC TGT CTG GCA        1310
Gln Arg Ile Glu Ile Ser Arg Arg Gly Asn Ala Gly Asp Cys Leu Ala
            300                 305                 310

AAC CCA GCA GTG CCC TGG GGA CAA GGT GTA GAA ATA GAA AGG GCC CTC        1358
Asn Pro Ala Val Pro Trp Gly Gln Gly Val Glu Ile Glu Arg Ala Leu
                315                 320                 325

AAA CAG GTT CAG GTT GAA GGT CTC TCA GGA AAT ATA AAG TTT GAC CAG        1406
Lys Gln Val Gln Val Glu Gly Leu Ser Gly Asn Ile Lys Phe Asp Gln
            330                 335                 340

AAT GGA AAA AGA ATA AAC TAT ACA ATT AAC ATC ATG GAG CTC AAA ACT        1454
Asn Gly Lys Arg Ile Asn Tyr Thr Ile Asn Ile Met Glu Leu Lys Thr
345                 350                 355                 360

AAT GGG CCC CGG AAG ATT GGC TAC TGG AGT GAA GTG GAC AAA ATG GTT        1502
Asn Gly Pro Arg Lys Ile Gly Tyr Trp Ser Glu Val Asp Lys Met Val
                365                 370                 375

GTT ACC CTT ACT GAG CTC CCT TCT GGA AAT GAC ACC TCT GGG CTT GAG        1550
Val Thr Leu Thr Glu Leu Pro Ser Gly Asn Asp Thr Ser Gly Leu Glu
            380                 385                 390

AAT AAG ACT GTT GTT GTC ACC ACA ATT TTG GAA TCT CCG TAT GTT ATG        1598
Asn Lys Thr Val Val Val Thr Thr Ile Leu Glu Ser Pro Tyr Val Met
            395                 400                 405

ATG AAG AAA AAT CAT GAA ATG CTT GAA GGC AAT GAG CGC TAT GAG GGC        1646
Met Lys Lys Asn His Glu Met Leu Glu Gly Asn Glu Arg Tyr Glu Gly
            410                 415                 420

TAC TGT GTT GAC CTG GCT GCA GAA ATC GCC AAA CAT TGT GGG TTC AAG        1694
Tyr Cys Val Asp Leu Ala Ala Glu Ile Ala Lys His Cys Gly Phe Lys
425                 430                 435                 440

TAC AAG TTG ACA ATT GTT GGT GAT GGC AAG TAT GGG GCC AGG GAT GCA        1742
Tyr Lys Leu Thr Ile Val Gly Asp Gly Lys Tyr Gly Ala Arg Asp Ala
                445                 450                 455

GAC ACG AAA ATT TGG AAT GGG ATG GTT GGA GAA CTT GTA TAT GGG AAA        1790
Asp Thr Lys Ile Trp Asn Gly Met Val Gly Glu Leu Val Tyr Gly Lys
            460                 465                 470

GCT GAT ATT GCA ATT GCT CCA TTA ACT ATT ACC CTT GTG AGA GAA GAG        1838
Ala Asp Ile Ala Ile Ala Pro Leu Thr Ile Thr Leu Val Arg Glu Glu
            475                 480                 485

GTG ATT GAC TTC TCA AAG CCC TTC ATG AGC CTC GGG ATA TCT ATC ATG        1886
Val Ile Asp Phe Ser Lys Pro Phe Met Ser Leu Gly Ile Ser Ile Met
            490                 495                 500

ATC AAG AAG CCT CAG AAG TCC AAA CCA GGA GTG TTT TCC TTT CTT GAT        1934
Ile Lys Lys Pro Gln Lys Ser Lys Pro Gly Val Phe Ser Phe Leu Asp
505                 510                 515                 520

CCT TTA GCC TAT GAG ATC TGG ATG TGC ATT GTT TTT GCC TAC ATT GGG        1982
Pro Leu Ala Tyr Glu Ile Trp Met Cys Ile Val Phe Ala Tyr Ile Gly
                525                 530                 535

GTC AGT GTA GTT TTA TTC CTG GTC AGC AGA TTT AGC CCC TAC GAG TGG        2030
Val Ser Val Val Leu Phe Leu Val Ser Arg Phe Ser Pro Tyr Glu Trp
            540                 545                 550

CAC ACT GAG GAG TTT GAA GAT GGA AGA GAA ACA CAA AGT AGT GAA TCA        2078
His Thr Glu Glu Phe Glu Asp Gly Arg Glu Thr Gln Ser Ser Glu Ser
            555                 560                 565

ACT AAT GAA TTT GGG ATT TTT AAT AGT CTC TGG TTT TCC TTG GGT GCC        2126
Thr Asn Glu Phe Gly Ile Phe Asn Ser Leu Trp Phe Ser Leu Gly Ala
570                 575                 580

TTT ATG CGG CAA GGA TGC GAT ATT TCG CCA AGA TCC CTC TCT GGG CGC        2174
Phe Met Arg Gln Gly Cys Asp Ile Ser Pro Arg Ser Leu Ser Gly Arg
585                 590                 595                 600
```

-continued

```
ATT GTT GGA GGT GTG TGG TGG TTC TTT ACC CTG ATC ATA ATC TCC TCC    2222
Ile Val Gly Gly Val Trp Trp Phe Phe Thr Leu Ile Ile Ile Ser Ser
                605                     610                 615

TAC ACG GCT AAC TTA GCT GCC TTC CTG ACT GTA GAG AGG ATG GTG TCT    2270
Tyr Thr Ala Asn Leu Ala Ala Phe Leu Thr Val Glu Arg Met Val Ser
            620                     625                 630

CCC ATC GAA AGT GCT GAG GAT CTT TCT AAG CAA ACA GAA ATT GCT TAT    2318
Pro Ile Glu Ser Ala Glu Asp Leu Ser Lys Gln Thr Glu Ile Ala Tyr
                635                     640                 645

GGA ACA TTA GAC TCT GGC TCC ACT AAA GAG TTT TTC AGG AGA TCT AAA    2366
Gly Thr Leu Asp Ser Gly Ser Thr Lys Glu Phe Phe Arg Arg Ser Lys
            650                     655                 660

ATT GCA GTG TTT GAT AAA ATG TGG ACC TAC ATG CGG AGT GCG GAG CCC    2414
Ile Ala Val Phe Asp Lys Met Trp Thr Tyr Met Arg Ser Ala Glu Pro
665                     670                     675             680

TCT GTG TTT GTG AGG ACT ACG GCC GAA GGG GTG GCT AGA GTG CGG AAG    2462
Ser Val Phe Val Arg Thr Thr Ala Glu Gly Val Ala Arg Val Arg Lys
                685                     690                 695

TCC AAA GGG AAA TAT GCC TAC TTG TTG GAG TCC ACG ATG AAC GAG TAC    2510
Ser Lys Gly Lys Tyr Ala Tyr Leu Leu Glu Ser Thr Met Asn Glu Tyr
            700                     705                 710

ATT GAG CAA AGG AAG CCT TGC GAC ACC ATG AAA GTT GGT GGA AAC CTG    2558
Ile Glu Gln Arg Lys Pro Cys Asp Thr Met Lys Val Gly Gly Asn Leu
                715                     720                 725

GAT TCC AAA GGC TAT GGC ATC GCA ACA CCT AAA GGA TCC TCA TTA GGA    2606
Asp Ser Lys Gly Tyr Gly Ile Ala Thr Pro Lys Gly Ser Ser Leu Gly
            730                     735                 740

ACC CCA GTA AAT CTT GCA GTA TTG AAA CTC AGT GAG CAA GGC GTC TTA    2654
Thr Pro Val Asn Leu Ala Val Leu Lys Leu Ser Glu Gln Gly Val Leu
745                     750                     755             760

GAC AAG CTG AAA AAC AAA TGG TGG TAC GAT AAA GGT GAA TGT GGA GCC    2702
Asp Lys Leu Lys Asn Lys Trp Trp Tyr Asp Lys Gly Glu Cys Gly Ala
                765                     770                 775

AAG GAC TCT GGA AGT AAG GAA AAG ACC AGT GCC CTC AGT CTG AGC AAC    2750
Lys Asp Ser Gly Ser Lys Glu Lys Thr Ser Ala Leu Ser Leu Ser Asn
            780                     785                 790

GTT GCT GGA GTA TTC TAC ATC CTT GTC GGG GGC CTT GGT TTG GCA ATG    2798
Val Ala Gly Val Phe Tyr Ile Leu Val Gly Gly Leu Gly Leu Ala Met
            795                     800                 805

CTG GTG GCT TTG ATT GAG TTC TGT TAC AAG TCA AGG GCC GAG GCG AAA    2846
Leu Val Ala Leu Ile Glu Phe Cys Tyr Lys Ser Arg Ala Glu Ala Lys
            810                     815                 820

CGA ATG AAG GTG GCA AAG AAT GCA CAG AAT ATT AAC CCA TCT TCC TCG    2894
Arg Met Lys Val Ala Lys Asn Ala Gln Asn Ile Asn Pro Ser Ser Ser
825                     830                     835             840

CAG AAT TCA CAG AAT TTT GCA ACT TAT AAG GAA GGT TAC AAC GTA TAT    2942
Gln Asn Ser Gln Asn Phe Ala Thr Tyr Lys Glu Gly Tyr Asn Val Tyr
                845                     850                 855

GGC ATC GAA AGT GTT AAA ATT TAGGGGATGA CCTTGAATGA TGCCATGAGG       2993
Gly Ile Glu Ser Val Lys Ile
                860

AACAAGGCAA GGCTGTCAAT TACAGGAAGT ACTGGAGAAA ATGGACGTGT TATGACTCCA  3053

GAATTTCCCA AAGCNGTGCA TGCTGTCCCT TACGTGAGTC CTGGCATGGG AATGAATGTC  3113

AGTGTGACTG ATCTCTCGTG ATTGATAAGA ACCTTTTGAG TGCCTTACAC AATGGTTTTC  3173

TTGTGTGTTT ATTGTCAAAG TGGTGAGAGG CATCCAGTAT CTTGAAGACT TTTCTTTCAG  3233

CCAAGAATTC TTAAATATGT GGAGTTCATC TTGAATTGTA AGGAATGATT AATTAAAACA  3293
```

```
CAACATCTTT TTCTACTCGA GTTACAGACA AAGCGTGGTG GACATGCACA GCTAACATGG    3353

AAGTACTATA ATTTACCTGA AGTCTTTGTA CAGACAACAA ACCTGTTTCT GCAG          3407
```

(2) INFORMATION FOR SEQ ID NO:2:

(i) SEQUENCE CHARACTERISTICS:
        (A) LENGTH: 883 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Lys Ile Met His Ile Ser Val Leu Leu Ser Pro Val Leu Trp
-20              -15                 -10                  -5

Gly Leu Ile Phe Gly Val Ser Ser Asn Ser Ile Gln Ile Gly Gly Leu
              1               5                  10

Phe Pro Arg Gly Ala Asp Gln Glu Tyr Ser Ala Phe Arg Val Gly Met
            15                  20                  25

Val Gln Phe Ser Thr Ser Glu Phe Arg Leu Thr Pro His Ile Asp Asn
        30                  35                  40

Leu Glu Val Ala Asn Ser Phe Ala Val Thr Asn Ala Phe Cys Ser Gln
45                  50                  55                  60

Phe Ser Arg Gly Val Tyr Ala Ile Phe Gly Phe Tyr Asp Lys Lys Ser
                65                  70                  75

Val Asn Thr Ile Thr Ser Phe Cys Gly Thr Leu His Val Ser Phe Ile
            80                  85                  90

Thr Pro Ser Phe Pro Thr Asp Gly Thr His Pro Phe Val Ile Gln Met
        95                  100                 105

Arg Pro Asp Leu Lys Gly Ala Leu Leu Ser Leu Ile Glu Tyr Tyr Gln
110                 115                 120

Trp Asp Lys Phe Ala Tyr Leu Tyr Asp Ser Asp Arg Gly Leu Ser Thr
125                 130                 135                 140

Leu Gln Ala Val Leu Asp Ser Ala Ala Glu Lys Lys Trp Gln Val Thr
                145                 150                 155

Ala Ile Asn Val Gly Asn Ile Asn Asn Asp Lys Lys Asp Glu Met Tyr
            160                 165                 170

Arg Ser Leu Phe Gln Asp Leu Glu Leu Lys Lys Glu Arg Arg Val Ile
        175                 180                 185

Leu Asp Cys Glu Arg Asp Lys Val Asn Asp Ile Val Asp Gln Val Ile
    190                 195                 200

Thr Ile Gly Lys His Val Lys Gly Tyr His Tyr Ile Ile Ala Asn Leu
205                 210                 215                 220

Gly Phe Thr Asp Gly Asp Leu Leu Lys Ile Gln Phe Gly Gly Ala Asn
                225                 230                 235

Val Ser Gly Phe Gln Ile Val Asp Tyr Asp Asp Ser Leu Val Ser Lys
            240                 245                 250

Phe Ile Glu Arg Trp Ser Thr Leu Glu Glu Lys Glu Tyr Pro Gly Ala
        255                 260                 265

His Thr Thr Thr Ile Lys Tyr Thr Ser Ala Leu Thr Tyr Asp Ala Val
    270                 275                 280

Gln Val Met Thr Glu Ala Phe Arg Asn Leu Arg Lys Gln Arg Ile Glu
285                 290                 295                 300

Ile Ser Arg Arg Gly Asn Ala Gly Asp Cys Leu Ala Asn Pro Ala Val
                305                 310                 315
```

-continued

```
Pro Trp Gly Gln Gly Val Glu Ile Glu Arg Ala Leu Lys Gln Val Gln
            320                 325                 330
Val Glu Gly Leu Ser Gly Asn Ile Lys Phe Asp Gln Asn Gly Lys Arg
        335                 340                 345
Ile Asn Tyr Thr Ile Asn Ile Met Glu Leu Lys Thr Asn Gly Pro Arg
350                 355                 360
Lys Ile Gly Tyr Trp Ser Glu Val Asp Lys Met Val Val Thr Leu Thr
365                 370                 375                 380
Glu Leu Pro Ser Gly Asn Asp Thr Ser Gly Leu Glu Asn Lys Thr Val
                385                 390                 395
Val Val Thr Thr Ile Leu Glu Ser Pro Tyr Val Met Met Lys Lys Asn
            400                 405                 410
His Glu Met Leu Glu Gly Asn Glu Arg Tyr Glu Gly Tyr Cys Val Asp
        415                 420                 425
Leu Ala Ala Glu Ile Ala Lys His Cys Gly Phe Lys Tyr Lys Leu Thr
    430                 435                 440
Ile Val Gly Asp Gly Lys Tyr Gly Ala Arg Asp Ala Asp Thr Lys Ile
445                 450                 455                 460
Trp Asn Gly Met Val Gly Glu Leu Val Tyr Gly Lys Ala Asp Ile Ala
                465                 470                 475
Ile Ala Pro Leu Thr Ile Thr Leu Val Arg Glu Val Ile Asp Phe
            480                 485                 490
Ser Lys Pro Phe Met Ser Leu Gly Ile Ser Ile Met Ile Lys Lys Pro
        495                 500                 505
Gln Lys Ser Lys Pro Gly Val Phe Ser Phe Leu Asp Pro Leu Ala Tyr
    510                 515                 520
Glu Ile Trp Met Cys Ile Val Phe Ala Tyr Ile Gly Val Ser Val Val
525                 530                 535                 540
Leu Phe Leu Val Ser Arg Phe Ser Pro Tyr Glu Trp His Thr Glu Glu
                545                 550                 555
Phe Glu Asp Gly Arg Glu Thr Gln Ser Ser Glu Ser Thr Asn Glu Phe
            560                 565                 570
Gly Ile Phe Asn Ser Leu Trp Phe Ser Leu Gly Ala Phe Met Arg Gln
        575                 580                 585
Gly Cys Asp Ile Ser Pro Arg Ser Leu Ser Gly Arg Ile Val Gly Gly
    590                 595                 600
Val Trp Trp Phe Phe Thr Leu Ile Ile Ile Ser Ser Tyr Thr Ala Asn
605                 610                 615                 620
Leu Ala Ala Phe Leu Thr Val Glu Arg Met Val Ser Pro Ile Glu Ser
                625                 630                 635
Ala Glu Asp Leu Ser Lys Gln Thr Glu Ile Ala Tyr Gly Thr Leu Asp
            640                 645                 650
Ser Gly Ser Thr Lys Glu Phe Phe Arg Arg Ser Lys Ile Ala Val Phe
        655                 660                 665
Asp Lys Met Trp Thr Tyr Met Arg Ser Ala Glu Pro Ser Val Phe Val
    670                 675                 680
Arg Thr Thr Ala Glu Gly Val Ala Arg Val Arg Lys Ser Lys Gly Lys
685                 690                 695                 700
Tyr Ala Tyr Leu Leu Glu Ser Thr Met Asn Glu Tyr Ile Glu Gln Arg
                705                 710                 715
Lys Pro Cys Asp Thr Met Lys Val Gly Gly Asn Leu Asp Ser Lys Gly
            720                 725                 730
Tyr Gly Ile Ala Thr Pro Lys Gly Ser Ser Leu Gly Thr Pro Val Asn
```

-continued

```
                    735                 740                 745
Leu Ala Val Leu Lys Leu Ser Glu Gln Gly Val Leu Asp Lys Leu Lys
    750                 755                 760

Asn Lys Trp Trp Tyr Asp Lys Gly Glu Cys Gly Ala Lys Asp Ser Gly
765                 770                 775                 780

Ser Lys Glu Lys Thr Ser Ala Leu Ser Leu Ser Asn Val Ala Gly Val
                785                 790                 795

Phe Tyr Ile Leu Val Gly Gly Leu Gly Leu Ala Met Leu Val Ala Leu
                800                 805                 810

Ile Glu Phe Cys Tyr Lys Ser Arg Ala Glu Ala Lys Arg Met Lys Val
            815                 820                 825

Ala Lys Asn Ala Gln Asn Ile Asn Pro Ser Ser Ser Gln Asn Ser Gln
    830                 835                 840

Asn Phe Ala Thr Tyr Lys Glu Gly Tyr Asn Val Tyr Gly Ile Glu Ser
845                 850                 855                 860

Val Lys Ile (2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other nucleic acid;
         (A) DESCRIPTION: Synthetic DNA oligonucleotide (xi) SEQUENCE DESCRIPTION: SEQ ID NO:3:

GTGAATGTGG AGCCAAGGAC TCGGGAAGTA AG                                    32
```

AMPA-BINDING HUMAN GLUR2 RECEPTORS

This application is a divisional of application Ser. No. 08/242,344, filed May 13, 1994, which is a continuation of application Ser. No. 07/896,437, filed Jun. 10, 1992, abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impluses is controlled by the interaction between a neurotransmitter substance released by the "sending" neuron which binds to a surface receptor on the "receiving" neuron to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered. Hollmann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettler et al., Neuron 5: 583, 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gene. These authors, as well as Monyer et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

SUMMARY OF THE INVENTION

The present invention provides an isolated polynucleotide that codes for an AMPA-binding human EAA receptor. By providing polynucleotide that codes specifically for a CNS receptor native to humans, the present invention provides means for evaluating the human nervous system, and particularly for assessing potentially therapeutic interactions between the AMPA-binding human EAA receptors and selected natural and synthetic ligands.

In one of its aspects, the present invention provides an isolated polynucleotide comprising nucleic acids arranged in a sequence that encodes for the human EAA receptor herein designated the human GluR2B receptor. Alternatively, the polynucleotide may code for an AMPA-binding fragment of the human GluR2B receptor, or for an AMPA-binding variant of the human GluR2B receptor. In various specific embodiments of the present invention, the polynucleotide consists of DNA e.g. cDNA, or of RNA e.g. messenger RNA. In other embodiments of the present invention, the polynucleotide may be coupled to a reporter molecule, such as a radioactive label, for use in autoradiographic studies of human GluR2B receptor tissue distribution. In further embodiments of the present invention, fragments of the polynucleotides of the invention, including radiolabelled versions thereof, may be employed either as probes for detection of glutamate receptor-encoding polynucleotides, as primers appropriate for amplifying such polynucleotides present in a biological specimen, or as templates for expression of GluR2B receptor or an AMPA-binding fragment or variant thereof.

According to another aspect of the present invention, there is provided a cellular host having incorporated therein a polynucleotide of the present invention. In embodiments of the present invention, the polynucleotide is a DNA molecule and is incorporated for expression and secretion in the cellular host, to yield a functional, membrane-bound human GluR2B receptor. In other embodiments of the present invention, the polynucleotide is an RNA molecule which is incorporated in the cellular host to yield the human GluR2B receptor as a functional, membrane-bound product of translation.

According to another aspect of the invention, there is provided a process for obtaining a substantially homogeneous source of a human EAA receptor useful for performing ligand binding assays, which comprises the steps of culturing a genetically engineered cellular host of the invention, and then recovering the cultured cells. Optionally, the cultured cells may be treated to obtain membrane preparations thereof, for use in the ligand binding assays.

According to another aspect of the present invention, there is provided a method for assaying a substance for binding to a human EAA receptor, in which the substance is incubated under appropriate conditions with a human GluR2B receptor source, i.e., a cellular host of the invention or a membrane preparation derived therefrom, and then determining the extent of binding between the substance and the receptor source.

These and other aspects of the invention are now described in greater detail with reference to the accompanying drawings, in which:

BRIEF DESCRIPTION OF THE DRAWINGS

FIGS. 1(A)–1(K) provide a DNA sequence (SEQ ID NO:1) coding for the human GluR2B receptor, and the amino acid sequence (SEQ ID NO:2) thereof;

FIG. 4 illustrates the AMPA-binding property of the human GluR2B receptor.

DETAILED DESCRIPTION OF THE INVENTION AND ITS PREFERRED EMBODIMENTS

Figure 2:
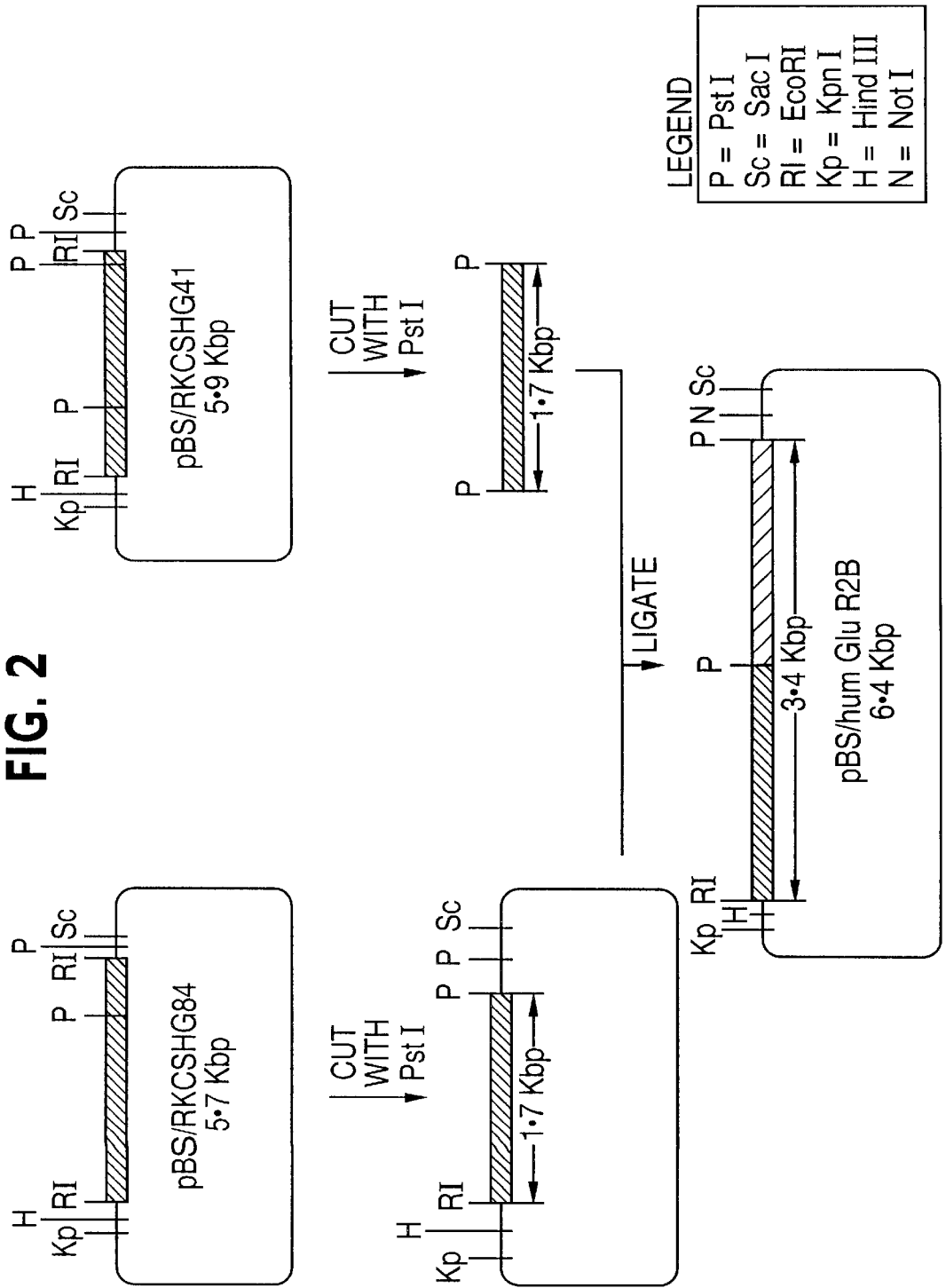
FIG. 2 depicts the strategy employed in cloning the human GluR2B receptor-encoding DNA illustrated in FIGS. 1(A)–1(K)
Figure 3:
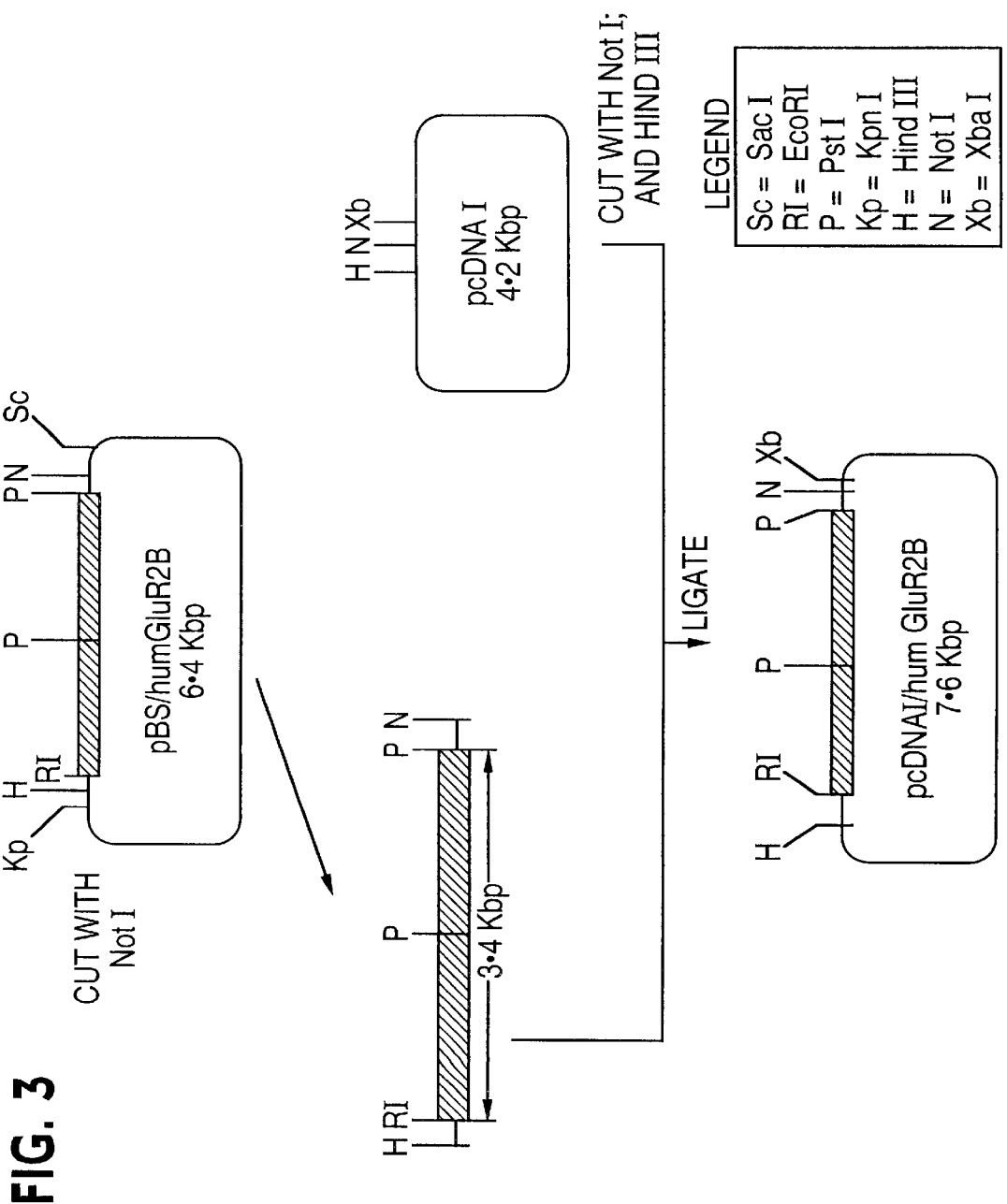
FIG. 3 depicts the strategy employed in generating recombinant DNA expression constructs incorporating the receptor-encoding DNA.

The invention relates to human CNS receptors of the AMPA-binding type, and provides isolated polynucleotides that code for such receptors. The term "isolated" is used herein with reference to intact polynucleotides that are generally less than about 4,000 nucleotides in length, more suitably less than about 3,000 nucleotides in length, and which are otherwise isolated from DNA coding for other human proteins.

In the present context, human CNS receptors of the AMPA-binding type exhibit a characteristic ligand binding profile, which reveals glutamate binding and relatively greater affinity for binding AMPA than for binding other CNS receptor ligands such as kainate, glutamate and their closely related analogues.

In the present specification, an AMPA-binding receptor is said to be "functional" if a cellular host producing it exhibits de novo channel activity when exposed appropriately to AMPA, as determined by the established electrophysiological assays described for example by Hollman et al, supra, or by any other assay appropriate for detecting conductance across a cell membrane.

The human GluR2B receptor of the invention possess structural features characteristic of the EAA receptors in general, including extracellular N- and C-terminal regions, as well as four internal hydrophobic domains which serve to anchor the receptor within the cell surface membrane. More specifically, GluR2B receptor is a protein characterized structurally as a single polypeptide chain that is produced initially in precursor form bearing a 21 amino acid residue N-terminal signal peptide, and is transported to the cell surface in mature form, lacking the signal peptide and consisting of 862 amino acids arranged in the sequence illustrated, by single letter code, in FIGS. 1(A)–1(K) (SEQ ID NO:1 and 2). Unless otherwise stated, the term human GluR2B receptor refers to the mature form of the receptor, and amino acid residues of the human GluR2B receptor are accordingly numbered with reference to the mature protein sequence. With respect to structural domains of the receptor, hydropathy analysis reveals four putative transmembrane domains, one spanning residues 525–544 inclusive (TM-1), another spanning residues 571–589 (TM-2), a third spanning residues 600–618 (TM-3) and the fourth spanning residues 792–812 (TM-4). Based on this assignment, it is likely that the human GluR2B receptor structure, in its natural membrane-bound form, consists of a 524 amino acid N-terminal extracellular domain, followed by a hydrophobic region containing four transmembrane domains and an extracellular, 50 amino acid C-terminal domain.

Binding assays performed with various ligands, and with membrane preparations derived from mammalian cells engineered genetically to produce the human GluR2B receptor in membrane-bound form indicate that GluR2B binds selectively to AMPA, relative particularly to kainate and NMDA. This feature, coupled with the medically significant connection between AMPA-type receptors and neurological disorders and disease indicate that the present receptor, and AMPA-binding fragments and variants thereof, will serve as valuable tools in the screening and discovery of ligands useful to modulate in vivo interactions between such receptors and their natural ligand, glutamate. Thus, a key aspect of the present invention resides in the construction of cells that are engineered genetically to produce human GluR2B receptor, to serve as a ready and homogeneous source of receptor for use in in vitro ligand binding and/or channel activation assays.

For use in the ligand binding assays, it is desirable to construct by application of genetic engineering techniques a mammalian cell that produces human GluR2B receptor as a heterologous, membrane-bound product. According to one embodiment of the invention, the construction of such engineered cells is achieved by introducing into a selected host cell a recombinant DNA construct in which DNA coding for a secretable form of the human GluR2B receptor, i.e. a form bearing its native signal peptide or a functional, heterologous equivalent thereof, is linked operably with expression controlling elements that are functional in the selected host to drive expression of the receptor-encoding DNA, and thus elaborate the desired human GluR2B receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human GluR2B receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevetheless serve as expression hosts, provided that "background" binding to the test ligand is accounted for in the assay results.

According to one embodiment of the present invention, the cell line selected to serve as host for human GluR2B receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the human GluR3 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the receptor in secretable form is linked with expression controlling DNA sequences recognized by the host, and which include a region 5' of the receptor-encoding DNA to drive expression, and a 3' region to terminate expression. The plasmidic vector harbouring the recombinant DNA expression construct typically incorporates such other functional components as an origin of replication, usually virally-derived, to permit replication of the plasmid in the expression host and desirably also for plasmid amplification in a bacterial host, such as E.coli. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e. the metalothionein gene promoter, and other steroid-inducible promoters.

For incorporation into the recombinant DNA expression vector, DNA coding for the human GluR2B receptor, or an AMPA-binding fragment or variant thereof, can be obtained by applying selected techniques of gene isolation or gene synthesis. As described in more detail in the examples herein, the human GluR28B receptor is encoded within the genome of human brain tissue, and can therefore be obtained from human DNA libraries by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in for example a bacterial plasmid, more typically a bacteriophage. Such bacteriophage harbouring fragments of the human DNA are typically grown by plating on a lawn of susceptible E. coli bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

In a specific embodiment of the invention, the GluR2B receptor is encoded by the DNA sequence (SEQ ID NO:1) illustrated in FIGS. 1(A)–1(K). In an obvious alternative, the DNA sequences coding for the selected receptor may be a synonymous codon equivalent of the illustrated DNA sequences.

The illustrated DNA sequence constitutes the cDNA sequence identified in human brain cDNA libraries in the manner exemplified herein. Having herein provided the nucleotide sequence of the human GluR2B receptor, however, it will be appreciated that polynucleotides encoding the receptor can be obtained by other routes. Automated techniques of gene synthesis and/or amplification can be performed to generate DNA coding therefor. Because of the length of the human GluR2B receptor-encoding DNA, application of automated synthesis may require staged gene construction, in which regions of the gene up to about 300 nucleotides in length are synthesized individually and then ligated in correct succession by overhang complementarity for final assembly. Individually synthesized gene regions can be amplified prior to assembly, using established polymerase chain reaction (PCR) technology.

The application of automated gene synthesis techniques provides an opportunity for generating polynucleotides that encode variants of the naturally occurring human GluR2B receptor. It will be appreciated, for example, that polynucleotides coding for the receptor can be generated by substituting synonymous codons for those represented in the naturally occurring polynucleotide sequences herein identified. In addition, polynucleotides coding for human GluR2B receptor variants can be generated which for example incorporate one or more, e.g. 1–10, single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR– cells into DHFR+ cells, and the tk gene of herpes simplex virus, which makes TK– cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The interaction e.g. the binding, of a substance, i.e., a test ligand, to human GluR2B receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to AMPA. This competitive binding assay can be performed by incubating the membrane preparation with radiolabelled AMPA, for example [3H]-AMPA, in the presence of unlabelled test compound added at varying concentrations. Following incubation, either displaced or bound radiolabelled AMPA can be recovered and measured, to determine the relative binding affinities of the test compound and AMPA for the particular receptor used as substrate. In this way, the affinities of various compounds for the AMPA-binding human EAA receptors can be measured. Alternatively, a radiolabelled analogue of glutamate may be employed in place of radiolabelled AMPA, as competing ligand.

As an alternative to using cells that express receptor-encoding DNA, ligand characterization may also be performed using cells for example *Xenopus oocytes*, that yield functional membrane-bound receptor following introduction by injection either of receptor-encoding messenger RNA into the oocyte cytoplasm, or of receptor-encoding DNA into the oocyte nucleus. To generate the messenger RNA of cytoplasmic delivery, the receptor-encoding DNA is typically subcloned first into a plasmidic vector adjacent a suitable promoter region, such as the T3 or T7 bacteriophage promoters, to enable transcription into RNA message. RNA is then transcribed from the inserted gene in vitro, collected and then injected into *Xenopus oocytes*. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell, in the established manner.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the human GluR2B receptor responsible for AMPA-binding resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length human GluR receptor-encoding DNA may be modified by site-directed mutagenesis, so as to introduce a translational stop codon into the extracellular N-terminal region, immediately before the sequence encoding the first transmembrane domain (TM1), i.e., before residue 525 as shown in FIGS. 1(A)–1(K) (SEQ ID NOS. 1 and 2). Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 813–862 inclusive (FIG. 1) (SEQ ID NOS. 1 and 2). In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such AMPA-binding receptor fragments may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. *Aspergillus nidulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of a human GluR2B receptor, for example in brain tissue, the present invention also provides, in another of its aspects, labelled antibody to the human GluR2B receptor. To raise such antibodies, there may be used as immunogen either the intact, soluble receptor or an immunogenic fragment thereof, i.e. a fragment capable of eliciting an immune response, produced in a microbial or mammalian cell host as described above or by standard peptide synthesis techniques. Regions of human GluR2B receptor particularly suitable for use as immunogenic fragments include those corresponding in sequence to an extracellular region of the receptor, or a portion of the extracellular region, such as peptides consisting of residues 1–524 or a fragment thereof comprising at least about 10 residues, including particularly fragments containing residues 175–190 or 477–520; and peptides corresponding to the region between transmembrane domains TM-2 and TM-3, such as a peptide consisting of residues 589–600. Peptides consisting of the C-terminal domain (residues 813–862), or fragment thereof, may also be used for the raising of antibodies.

The raising of antibodies to the selected human GluR2B receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for a human GluR2B receptor, and selected regions thereof, may also be used, in accordance with another aspect of the present invention, as hybridization probes for example to identify sequence-related genes resident in the human or other mammalian genomes (or cDNA libraries) or to locate the human GluR2B-encoding DNA in a specimen, such as brain tissue. This can be done using either the intact coding region, or a fragment thereof having radiolabelled e.g. $^{32}$P, nucleotides incorporated therein. To identify the human GluR2B-encoding DNA in a specimen, it is desirable to use either the full length cDNA coding therefor, or a fragment which is unique thereto. With reference to FIG. 1 (SEQ ID NO:1), such nucleotide fragments include those comprising at least about 17 nucleic acids, and otherwise corresponding in sequence to a region coding for the extracellular N-terminal or C-terminal region of the receptor, or representing a 5'-untranslated or 3'-untranslated region thereof. Such oligonucleotide sequences, and the intact gene itself, may also be used of course to clone human GluR2B-related human genes, particularly cDNA equivalents thereof, by standard hybridization techniques.

EXAMPLE 1

Isolation of DNA Coding for the Human GluR2B Receptor

The particular strategy used to clone the human Glu2B receptor is depicted schematically in FIG. 2, and described in greater detail below.

cDNA coding for the human GluR2B receptor was identified by probing human hippocampal cDNA that was obtained as an EcoRI-based lambda phage library (lambda ZAP) from Stratagene Cloning Systems (La Jolla, Calif., U.S.A.). The cDNA library was screened using an oligonucleotide probe capable of annealing to the 3' region of the rat GluR2 receptor sequence reported by Keinanen et al, supra. The specific sequence (SEQ ID NO:3) of the 32-P-labelled probe is provided below:

5'-GTGAATGTGGAGCCAAGGACTCGGGAAGTAAG-3'

The hippocampal cDNA library was screened under the following hybridization conditions; 6×SSC, 25% formamide, 5% Dernhardt's solution, 0.5% SDS, 100 ug/ml denatured salmon sperm DNA, 42° C. Filters were washed with 2×SSC containing 0.5% SDS at 25° C. for 5 minutes, followed by a 15 minute wash at 50° C. with 2×SSC containing 0.5% SDS. The final wash was with 1×SSC containing 0.5% SDS at 50° C. for 15 minutes. Filters were exposed to X-ray film (Kodak) overnight. Of $10^6$ clones screened, only two cDNA inserts were identified, one about 2.7 kb and designated RKCSHG84 and another about 2.9 kb and designated RKCSHG41 (FIG. 2). For sequencing, the '84 and the '41 phages were plaque purified, then excised as phagemids according to the supplier's specifications, to generate insert-carrying Bluescript-SK variants of the phagemid vector. Sequencing of the '84 clone across its entire sequence revealed a putative ATG initiation codon together with about 314 bases of 5' non-coding region and about 2.4 kb of coding region. Sequencing across the '41 insert revealed a significant region of overlap with the '84 insert, and also revealed a termination codon not found in the '84 insert as well as about 441 bases of 3' non-translated sequence.

To provide the entire coding region in an intact clone, the strategy shown in FIG. 2 was employed, to generate the phagemid pBS/HumGluR2B which carries the hGluR2B-encoding DNA as a 3.4 kb EcoRI/PstI insert in a 3.0 kb Bluescript-SK phagemid background. The entire sequence of the EcoRI/PstI insert is provided in FIG. 1 (SEQ ID NO:1).

The 6.4 kb phagemid pBS/humGluR2B was deposited, under the terms of the Budapest Treaty, with the American Type Culture Collection in Rockville, Md. USA on Mar. 19, 1992, and has been assigned accession number ATCC 75217.

EXAMPLE 2

Construction of Genetically Engineered Cells Producing Human GluR2B Receptor

For transient expression in mammalian cells, cDNA coding for the human GluR2B receptor was incorporated into the mammalian expression vector pcDNA1, which is available commercially from Invitrogen Corporation (San Diego, Calif., USA; catalogue number V490-20). This is a multi-functional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and antisense RNA transcripts and a Col E1-like high copy plasmid origin. A polylinker is located appropriately downstream of the CMV promoter (and 3' of the T7 promoter).

To facilitate incorporation of the GluR2B receptor-encoding cDNA into an expression vector, a NotI site was introduced onto the 5' flank of the Bluescript-SK cDNA insert, and the cDNA insert was then released from pBS/humGluR2B as a 3.4 kb HindIII/NotI fragment, which was then incorporated at the HindIII/NotI sites in the pcDNAI polylinker. Sequencing across the junctions was performed, to confirm proper insert orientation in pcDNA1. The resulting plasmid, designated pcDNA1/humGluR2B, was then introduced for transient expression into a selected mammalian cell host, in this case the monkey-derived, fibroblast like cells of the COS-1 lineage (available from the American Type Culture Collection, Rockville, Md. as ATCC CRL 1650).

For transient expression of the GluR2B-encoding DNA, COS-1 cells were transfected with approximately 8 ug DNA (as pcDNA1/humGluR2B) per $10^6$ COS cells, by DEAE-mediated DNA transfection and treated with chloroquine according to the procedures described by Maniatis et al, supra. Briefly, COS-1 cells were plated at a density of $5 \times 10^6$ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 uM chloroquine, 10% NuSerum, DNA (0.4 mg/ml) in DMEM/F12 medium. After incubation for 3 hours at 37° C., cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also prepared using two different cell types as host: CHO K1 and CHO Pro5. To construct these cell lines, cDNA coding for human GluR2B was incorporated into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5 \times 10^5$ in 10% FBS-supplemented MEM medium. After growth for 24 hours, fresh medium are added to the plates and three hours later, the cells are transfected using the calcium phosphate-DNA co-precipitation procedure (Maniatis et al, supra). Briefly, 3 ug of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 3

Ligand Binding Assays

Transfected cells in the frozen state were resuspended in ice-cold distilted water using a hand homogenizer, sonicated for 5 seconds, and then centrifuged for 20 minutes at 50,000 g. The supernatant was discarded and the membrane pellet stored frozen at −70° C.

COS cell membrane pellets were suspended in ice cold 50 mM Tris-HCl (pH 7.55, 5° C.) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation was used as tissue source for binding experiments described below. Proteins were determined using the Pierce Reagent with BSA as standard.

Binding assays were then performed, using an amount of COS-derived membrane equivalent to from 25–100 ug as judged by protein determination and selected radiolabelled ligand. In particular, for AMPA-binding assays, incubation mixtures consisted of 25–100 ug tissue protein and D, L-alpha-[5-methyl-3H]amino-3-hydroxy-5-methylisoxazole-4-propionic acid (3H-AMPA, 27.6Ci/mmole, 10 nM final) with 0.1M KSCN and 2.5 mM $CaCl_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 4 ml of the cold incubation buffer, then 5 ml of Beckman Ready-Protein Plus scintillation cocktail was added, for counting.

For kainate-binding assays, incubation mixtures consisted of 25–100 ug tissue protein and [vinylidene-3H] kainic acid (58Ci/mmole, 5 nM final) in the cold incubation buffer, 1 ml final volume. Non-specific binding was determined in the presence of 1 mM L-glutamate. Samples were incubated as for the AMPA-binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Protein Plus scintillation cocktail for counting.

Assays performed in this manner, using membrane preparations derived from the human GluR2B receptor-producing COS cells, revealed specific binding of 750–850 fmole/mg protein, at 10 nM [3H]-AMPA (FIG. 4). Mock transfected cells exhibited no specific binding of any of the ligands tested. These results demonstrate clearly that the human GluR2B receptor is binding AMPA with specificity. This activity, coupled with the fact that there is little or no demonstrable binding of either kainate or NMDA, clearly assigns the human GluR2B receptor to be of the AMPA type of EAA receptor. Furthermore, this binding profile indicates that the receptor is binding in an authentic manner, and can therefore reliably predict the ligand binding "signature" of its non-recombinant counterpart from the human brain. These features make the recombinant receptor especially useful for selecting and characterizing ligand compounds which bind to the receptor, and/or for selecting and characterizing compounds which may act by displacing other ligands from the receptor. The isolation of the GluR2B receptor genes in substantially pure form, capable of being expressed as a single, homogeneous receptor species, therefore frees the ligand binding assay from the lack of precision introduced when complex, heterogeneous receptor preparations from human and other mammalian brains are used to attempt such characterizations.

We claim:

1. A membrane preparation derived from a host cell, said host cell having incorporated expressibly therein a heterologous polynucleotide that encodes human GluR2B receptor selected from the group consisting of: (a) the sequence of amino acids 1–863 of SEQ ID NO:2, (b) a human GluR2B receptor variant having a sequence of amino acids 1–863 of SEQ ID NO:2 with the exception that there are from 1–32 conservative amino acid substitutions, (c) a membrane-bound fragment of the human GluR2B receptor of (a) or (b) comprising the extracellular N-terminal region that precedes TM-1, and (d) a membrane-bound fragment of the human GluR2B receptor of (a) comprising the extracellular C-terminal region that follows TM-4.

2. A membrane preparation derived from a host cell as defined in claim 1, wherein the cellular host is a mammalian cell.

3. The human GluR2B receptor having the sequence of amino acids 1–863 of SEQ ID NO:2, in a form essentially free from other proteins of human origin.

4. A variant of a human GluR2B receptor, in a form essentially free from other proteins of human origin, which is a variant having a sequence of amino acids 1–863 of SEQ ID NO:2 with the exception that there are from 1–32 conservative amino acid substitutions.

5. An extracellular, immunogenic fragment of a human GluR2 receptor, wherein said receptor is selected from the group consisting of: (a) the sequence of amino acids 1–863 of SEQ ID NO:2, (b) a human GluR2B receptor variant of SEQ ID NO:2 having a sequence of amino acids 1–863 of SEQ ID NO:2 with the exception that there are from 1–32 conservative amino acid substitutions; and wherein said fragment is selected from the group consisting of: (i) the extracellular N-terminal region that precedes TM-1 of the human GluR2B receptor of (a) or (b), and (ii) the extracellular C-terminal region that follows TM-4 of the human GluR2B receptor of (a).

6. A fragment as claimed in claim 5, wherein said fragment comprises the extracellular N-terminal region.

7. A fragment as claimed in claim 6, wherein said fragment comprises the extracellular C-terminal region.

8. A fragment of a human GluR2B receptor comprising the extracellular N-terminal region that precedes TM-1 or the extracellular C-terminal region that follows TM-4 of human GluR2B, wherein the human GluR2B receptor has the sequence of amino acids 1–863 of SEQ ID NO:2.

9. An extracellular, immunogenic fragment of a human GluR2B receptor, wherein said fragment consists of residues 175–190 or 477–520 of SEQ ID NO:2.

* * * * *